June 12, 1956 H. C. SWIM Plant Pat. 1,482
PLUM TREE
Filed March 28, 1955
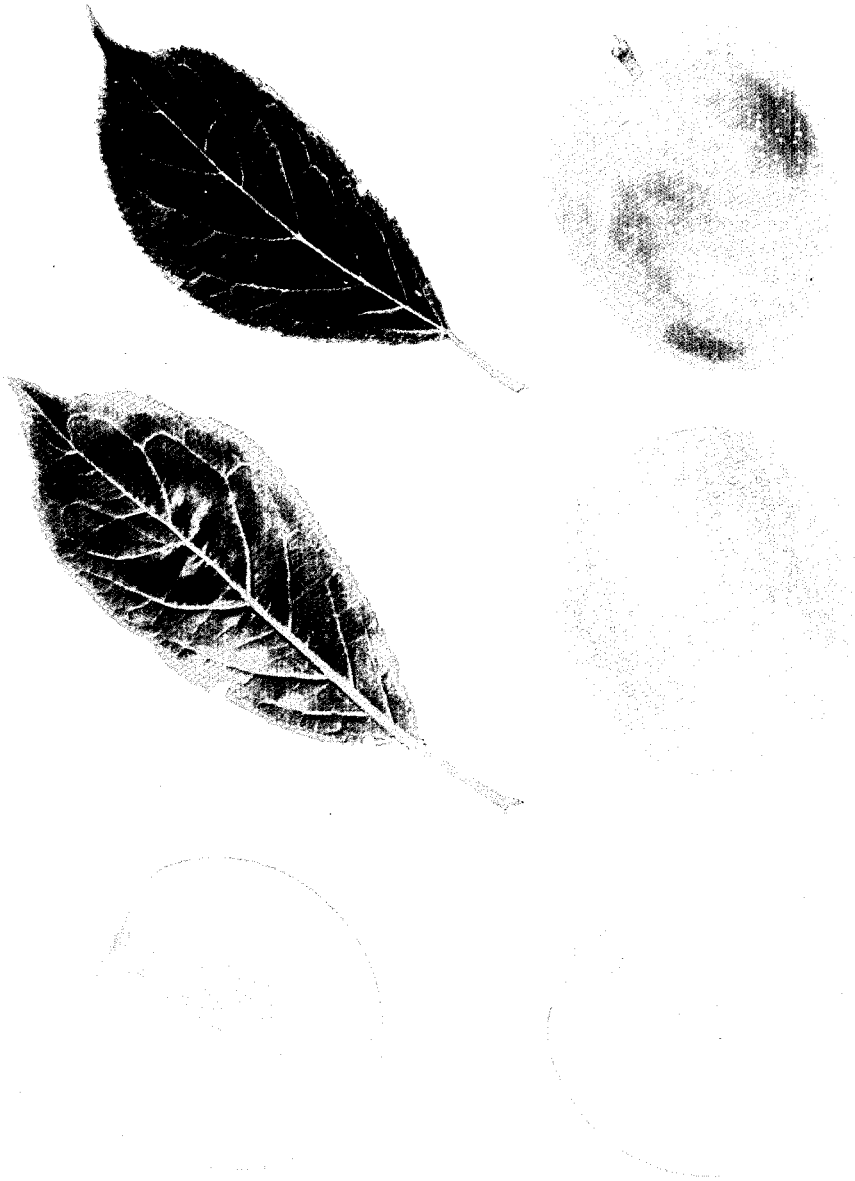
Inventor.
H. C. Swim
By: Robb & Robb
Attorneys.

United States Patent Office

Plant Pat. 1,482
Patented June 12, 1956

1,482

PLUM TREE

Herbert C. Swim, Ontario, Calif., assignor to Armstrong Nurseries, Inc., Ontario, Calif., a corporation of California Application March 28, 1955, Serial No. 497,483

1 Claim. (Cl. 47—62)

The present invention relates to a new and distinct variety of plum tree of the Japanese plum type which was originated by me by crossing the well-known "Inca" plum (unpatented) with the equally well-known variety "Santa Rosa" (unpatented).

The primary objective in making this cross was to endeavor to combine the most desirable characteristics of the parent varieties, and thus produce a new variety having a combination of characteristics that is more desirable than the characteristics found in either parent or in any other variety. This objective was fully achieved, as evidenced by the following principal characteristics which are outstanding in the new variety:

(1) A vigorous habit of growth comparable to that of the variety "Santa Rosa";

(2) The round shape of the fruit, as inherited from "Santa Rosa";

(3) The attractive and distinctive high color of the skin of the fruit, which is generally similar to that of "Santa Rosa";

(4) The firm, meaty, yellow flesh of the fruit, comparable to that of "Inca";

(5) The delectable flavor and the good eating and keeping qualities of the fruit, as inherited from the variety "Inca"; and (6) The semi-freestone habit of the fruit, as inherited from "Inca."

In comparison with its seed parent, "Inca," the skin of the fruit of my new variety is more highly colored; the fruit is more round in shape, as contrasted from the oval shape of the fruit of this parent; and the tree of my new variety is more vigorous than that of this parent.

As compared with its pollen parent, "Santa Rosa," the fruit of my new variety is sweeter in flavor; the flesh of the fruit is more free from the pit instead of clinging to the pit as in the variety "Santa Rosa"; and the flesh of the fruit of my new variety is more firm and meaty than that of this parent.

The foregoing features definitely distinguish my new variety from each parent, as well as from all other plum varieties of which I am aware, and asexual reproduction of the new variety by grafting, as performed by me at Ontario, California, shows that the foregoing characteristics and distinctions come true to form and are established and transmitted through succeeding propagations.

The accompanying illustration shows typical specimens of the foliage and fruit of my new variety as depicted in color as nearly true as it is reasonably possible to make the same in a color illustration of this character, both the upper and lower surfaces of a typical specimen leaf being illustrated in the drawing, and typical fruit specimens being shown in both elevation and cross-section, one of the sectional views showing the pit cavity, and the other sectional view exposing the pit.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious, as indicated:

Parentage:

*Seed parent.*—"Inca."

*Pollen parent.*—"Santa Rosa."

Propagation: Holds its distinguishing characteristics through succeeding propagations by grafting.

Locality where grown and observed: Ontario, California.

Dates of first and last picking: Vary somewhat from year-to-year because of varying winter chilling in Southern California, but usually begin picking from about June 24 to about July 25, and ending from about July 12 to about August 4, depending on the season.

Tree: Large; vigorous; upright; dense, vase-formed; productive; regular bearer.

*Trunk.*—Stocky; moderately rough.

*Branches.*—Medium in thickness; medium in smoothness; dull. Color—near Light Grayish Olive, Plate XLVI (Ridgway). Lenticels—Medium in number; from large to medium in size.

*Leaves.*—Length—from 3¼ inches to 4½ inches. Width—from 1¾ inches to 2½ inches. Size—large. Shape—long; obovate; acuminate; medium thickness; slightly rugose. Color: Upper side—near Forest Green, Plate XVII (Ridgway); under side—near Light Elm Green, Plate XVII (Ridgway). Margin—finely serrate; somewhat irregular. Petiole—medium length (approximately 1.5 cm.); from medium caliper to thick. Glands—average number—2, but some leaves have no glands; opposite; from small to medium size; globose to irregular; normally positioned at attachment of leaf blade to petiole. Color—green. Stipules—long; narrow.

*Flower-buds.*—Small; short; conic; pointed; glabrous.

*Flowers.*—Dates first and full bloom—beginning from about February 9 to about March 9, peaking from about February 17 to about March 16; early, as compared with other varieties. Size—considered as medium for plum varieties. Color—white.

Fruit:

*Maturity when described.*—Eating ripe; July 17.

*Size.*—Slightly variable; large. Axial diameter—from 1⅞ inches to 2 inches. Transverse diameter in suture plane—from 2 inches to 2⅛ inches. Diameter at right angles to suture plane—from 1⅞ inches to 2 inches.

*Form.*—Slightly variable; symmetrical; from broadly ovoid to round.

*Suture.*—An inconspicuous line extends from base to apex, but is discontinuous at apex.

*Ventral surface.*—Rounded. Lips—Suture lips lacking or very low and not protruding, but one lip sometimes is slightly larger than the other.

*Cavity.*—From rounded to somewhat elongated in suture plane, with suture showing on one side. Depth—⅛ inch. Breadth—from 5/16 inch to ⅜ inch. Markings—no unusual or distinctive markings.

*Base.*—Rounded.

*Apex.*—From rounded to truncate. Pistil point—slightly depressed.

*Stem.*—Length from ½ inch to ¾ inch; from medium caliper to stout; glabrous. Adherence to stone—medium.

*Skin.*—Medium thickness; tough; only slightly astringent; tenacious to flesh; no tendency to crack.

Color—between Dresden Yellow, Plate 64/2, page 64 (Wilson) and Primrose Yellow, Plate 601/2, page 65 (Wilson), heavily blushed with between Chrysanthemum Crimson, Plate 824/1, page 169 (Wilson) and Cardinal Red, Plate 822, page 168 (Wilson). Down—wanting, but a moderately heavy Grey bloom is apparent on skin.

*Flesh.*—Color—between Lemon Yellow, Plate 4/2, page 4 (Wilson) and Buttercup Yellow, Plate 5/2, page 5 (Wilson).

*Surface of pit cavity.*—Color—near Buttercup Yellow, Plate 5/2, page 5 (Wilson).

*Amygdalin.*—Scant.

*Juice.*—Abundant; rich.

*Texture.*—Firm; meaty.

*Fibers.*—Abundant; fine; tender.

*Ripens.*—Evenly.

*Flavor.*—From subacid to mild, giving a good blend of acid and sugar.

*Aroma.*—Not pronounced.

*Eating quality.*—Good.

Stone: Semi-free when fully ripe; adheres to flesh along both dorsal and ventral edges and in some places along sides, depending upon degree of ripeness of fruit.

*Fibers.*—Short.

*Size.*—Medium; length from 7/8 inch to 1 inch; breadth from 9/16 inch to 11/16 inch; thickness from 1/4 inch to 3/8 inch.

*Form.*—Long oval; cuneate toward apex.

*Base.*—Nearly straight; narrow hilum; acuminate apex.

*Sides.*—Nearly equal; curved on both sides; regular surface; longitudinal furrow at base; somewhat ridged near base.

*Ridges.*—Jagged.

*Pits.*—Elongated.

*Ventral edge.*—Thin.

*Dorsal edge.*—From medium to narrow, with narrow groove extending from base to apex; ridges on either side are more or less continuous.

*Tendency to split.*—None.

*Color.*—Between Cinnamon, Plate XXIX (Ridgway) and Pinkish Cinnamon, Plate XXIX (Ridgway).

Use: Market; local; dessert; shipping.

Keeping quality: Good.

Insect resistance: Medium resistance to thrips, as determined by comparison with other varieties grown under comparable cultural conditions at Ontario, California.

Disease resistance: Has shown no disease susceptibility, as yet, at Ontario, California.

Shipping quality: Good.

I claim:

A new and distinct variety of plum tree of the Japanese semi-freestone type, substantially as herein shown and described, characterized particularly as to novelty by its vigorous habit of growth, the roundness of its fruit, the attractive and distinctive color of the fruit skin, the firm, meaty, yellow flesh of the fruit, the delectable flavor and the good eating and keeping qualities of the fruit.

No references cited.